(12) United States Patent
Franzen

(10) Patent No.: US 8,651,229 B2
(45) Date of Patent: Feb. 18, 2014

(54) HEARING PROTECTION

(75) Inventor: Lars Peter Franzen, Helsingborg (SE)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/488,565

(22) Filed: Jun. 5, 2012

(65) Prior Publication Data
US 2013/0319788 A1 Dec. 5, 2013

(51) Int. Cl.
H04R 25/02 (2006.01)
A61F 11/14 (2006.01)
A61F 11/06 (2006.01)
H04R 25/00 (2006.01)
A61F 11/00 (2006.01)

(52) U.S. Cl.
USPC ........... 181/129; 381/371; 381/372; 381/373; 128/867

(58) Field of Classification Search
USPC ............ 181/129, 136; 381/72, 370, 371, 372, 381/373; 128/864, 867, 868; 2/209
See application file for complete search history.

(56) References Cited

U.S. PATENT DOCUMENTS

| 2,672,864 | A | * | 3/1954 | Makara | 128/866 |
| 2,782,423 | A | * | 2/1957 | Simon et al. | 2/209 |
| 3,117,575 | A | * | 1/1964 | Carrell et al. | 128/866 |
| 3,506,981 | A | * | 4/1970 | Stewart et al. | 2/209 |
| 3,602,329 | A | * | 8/1971 | Bauer et al. | 181/129 |
| 3,795,014 | A | * | 3/1974 | Simpson et al. | 2/209 |
| 3,842,829 | A | * | 10/1974 | Ellis | 128/868 |
| 3,908,200 | A | * | 9/1975 | Lundin | 2/209 |
| 3,922,725 | A | * | 12/1975 | Csiki et al. | 2/209 |
| 3,944,018 | A | * | 3/1976 | Satory | 181/175 |
| 4,037,273 | A | * | 7/1977 | Labaire | 2/209 |
| 4,041,256 | A | * | 8/1977 | Ohta et al. | 381/373 |
| 4,103,359 | A | * | 8/1978 | Rieppel et al. | 2/8.1 |
| 4,160,135 | A | * | 7/1979 | Gorike | 381/373 |
| 4,572,323 | A | * | 2/1986 | Randall | 181/129 |
| 4,670,911 | A | * | 6/1987 | Dunford | 2/209 |
| 4,674,134 | A | * | 6/1987 | Lundin | 2/209 |
| 4,807,612 | A | * | 2/1989 | Carlson | 128/868 |
| 4,809,811 | A | * | 3/1989 | Gorike | 181/129 |
| 4,924,502 | A | * | 5/1990 | Allen et al. | 381/72 |
| 5,241,971 | A | * | 9/1993 | Lundin | 128/864 |
| 5,970,160 | A |   | 10/1999 | Nilsson et al. | |
| 5,996,123 | A | * | 12/1999 | Leight et al. | 2/209 |
| RE37,398 | E | * | 10/2001 | Nageno | 381/371 |
| 6,353,938 | B1 | * | 3/2002 | Young | 2/209 |
| 6,831,984 | B2 | * | 12/2004 | Sapiejewski | 381/71.6 |

(Continued)

FOREIGN PATENT DOCUMENTS

DE 3119260 A1 6/1982
GB 1276498 6/1972
GB 2075849 A * 11/1981 ............ A61F 11/02

OTHER PUBLICATIONS

EP 13 16 9778; EP Search Report dated Sep. 6, 2013; 4 pages.

(Continued)

Primary Examiner — Edgardo San Martin
(74) Attorney, Agent, or Firm — Conley Rose, P.C.; Kristin Jordan Harkins

(57) ABSTRACT

Hearing protection devices are disclosed. One hearing protection device includes a first material, having sound attenuating characteristics, shaped to cover over an ear of a user; at least one aperture formed in the first material; and a second material positioned over the aperture.

20 Claims, 4 Drawing Sheets

(56) References Cited

U.S. PATENT DOCUMENTS

| | | | |
|---|---|---|---|
| 7,240,765 B2 * | 7/2007 | Berg et al. | 181/135 |
| 7,245,735 B2 * | 7/2007 | Han | 381/371 |
| 7,395,898 B2 * | 7/2008 | Yang et al. | 181/286 |
| 7,703,572 B2 * | 4/2010 | Du et al. | 181/129 |
| 7,717,226 B2 * | 5/2010 | Purcell et al. | 181/129 |
| 7,766,120 B2 * | 8/2010 | Hansson et al. | 181/129 |
| 8,249,285 B2 * | 8/2012 | Killion et al. | 381/372 |
| 2005/0126845 A1 | 6/2005 | Vaudrey et al. | |
| 2008/0017440 A1 * | 1/2008 | Seko et al. | 181/175 |
| 2009/0223738 A1 * | 9/2009 | Nakamura et al. | 181/175 |
| 2010/0218775 A1 | 9/2010 | Du et al. | |
| 2011/0240402 A1 * | 10/2011 | Chou et al. | 181/207 |

OTHER PUBLICATIONS

European Examination Report, Application No. EP 13 16 9778, dated Oct. 1, 2013; 4 pages.

* cited by examiner

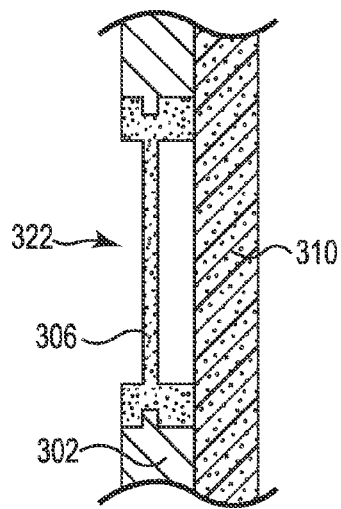
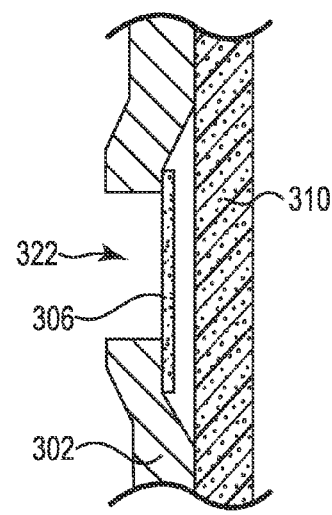
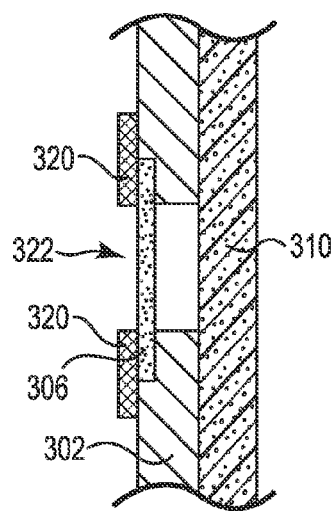
*Fig. 3A*     *Fig. 3B*     *Fig. 3C*
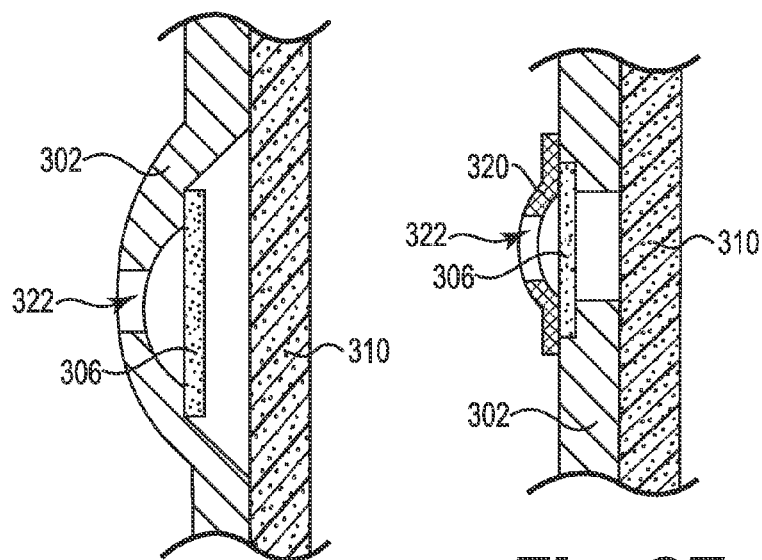
*Fig. 3D*     *Fig. 3E*

HEARING PROTECTION

TECHNICAL FIELD

The present disclosure relates to hearing protection.

BACKGROUND

Changes in legislation, such as arising from European Directive 2003/10/EC, make the use of hearing protection advisory for daily exposures at or above 80 dB, and compulsory where exposures exceed 85 dB. It may be assumed, therefore, that employers may be seeking personal hearing protection for workers in environments where noise levels are in the range 80-90 dB, and that employers are seeking to provide personal hearing protection to workers who have previously not made use of protection.

Employers should be seeking protection, suited to the work and working environment, but not 'over protecting' (i.e. aiming to avoid protected levels of less than 70 dB).

When worn in a noise environment of 85 dB, a protector providing attenuation equal to the minimum requirements would produce, according to standard methods and for the majority of the population, protected levels around or below the low to mid 70s (depending on the characteristics of the noise). Protected levels transpose correspondingly to higher or lower ambient levels.

However, there do not appear to be any devices on the market intended for occupational use, for example, that provide attenuation equal to or close to the minimum requirements described above. As a consequence, the market appears to fail the employer seeking a suitable protector for noise levels in the range 80-90 dB that does not 'overprotect'.

This overprotection can result in the user being afforded a non-trivial attenuation at low frequencies. Current solutions also may provide underprotection at lower frequencies and overprotection at higher frequencies. For example, some current devices provide almost zero dB attenuation up to 500 HZ and, then, 25 dB attenuation at higher frequencies.

BRIEF DESCRIPTION OF THE DRAWINGS

FIG. 3A illustrates another noise attenuating structure in accordance with one or more embodiments of the present disclosure.

FIG. 3B illustrates another noise attenuating structure in accordance with one or more embodiments of the present disclosure.

FIG. 3C illustrates another noise attenuating structure in accordance with one or more embodiments of the present disclosure.

FIG. 3D illustrates another noise attenuating structure in accordance with one or more embodiments of the present disclosure.

FIG. 3E illustrates another noise attenuating structure in accordance with one or more embodiments of the present disclosure.

DETAILED DESCRIPTION

Figure 1:
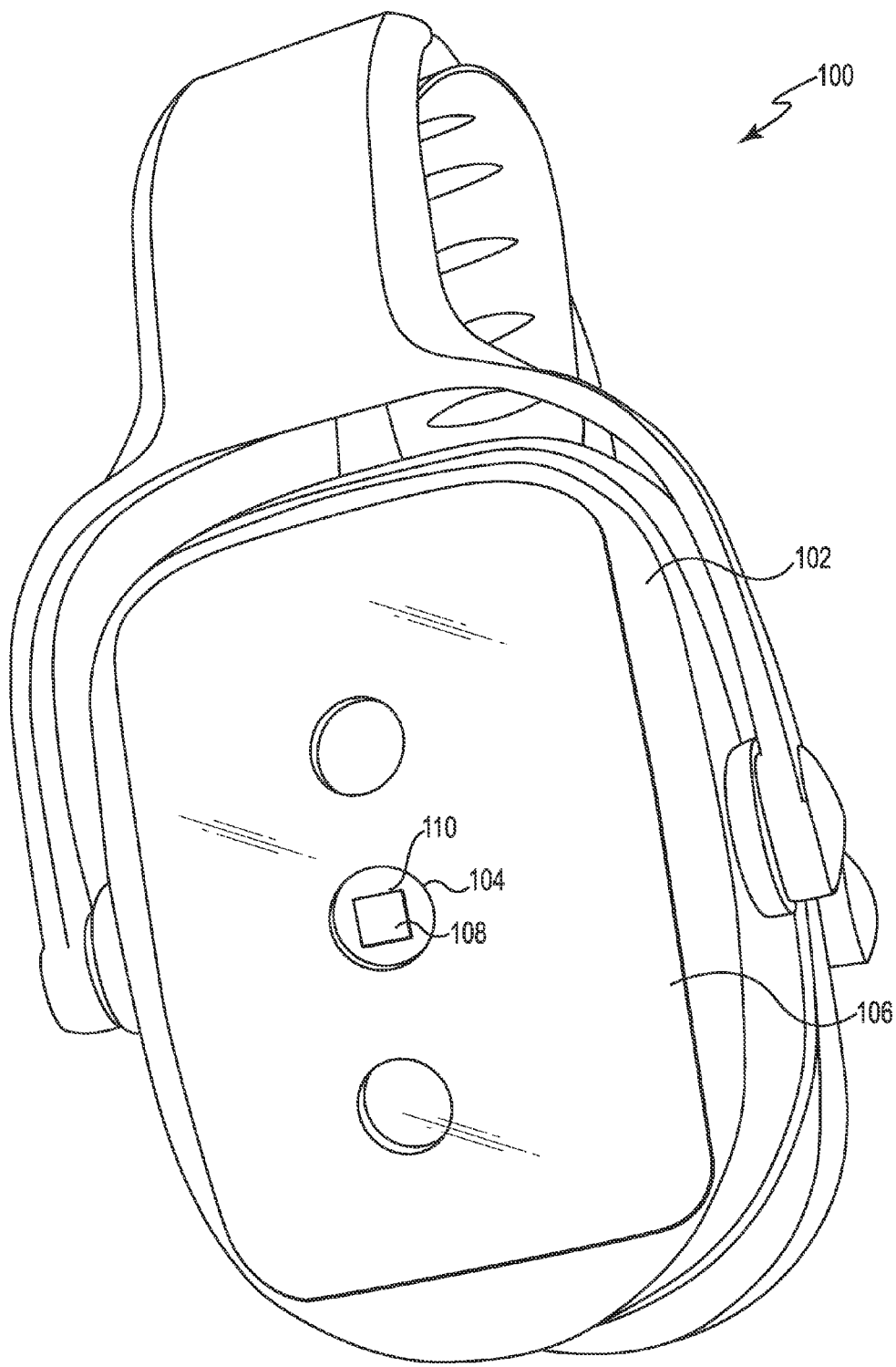
FIG. 1 illustrates a hearing protector in accordance with one or more embodiments of the present disclosure.

Hearing protection devices are disclosed. For example, one hearing protection device includes a first material, having sound attenuating characteristics, shaped to cover over an ear of a user; at least one aperture formed in the first material; and a second material positioned over the aperture. Such embodiments may provide better protection for the user, for example, by not overprotecting in the 80-90 dB range or underprotecting at lower frequencies (e.g., up to 500 Hz).

In the following detailed description, reference is made to the accompanying drawings that form a part hereof. The drawings show by way of illustration how one or more embodiments of the disclosure may be practiced. These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 104 may reference element "04" in FIG. 1, and a similar element may be referenced as 204 in FIG. 2A. As used herein, "a" or "a number of" something can refer to one or more such things. For example, "a number of apertures" can refer to one or more apertures.

FIG. 1 illustrates a hearing protector in accordance with one or more embodiments of the present disclosure. In the embodiment of FIG. 1, the device 100 includes a first material 102 having a number of apertures 104, a second material 106 wherein a portion of the second material 106 is positioned over the apertures 104, a third material 110, and a weight 108. These components will be discussed in more detail below.

In the embodiment of FIG. 1, the first material portion 102 has sound attenuating characteristics and is shaped to cover over an ear of a user. The third material portion 110 can be formed from any suitable material. As shown in the embodiment of FIG. 1, such devices typically include one portion that is shaped to fit over one ear and another portion shaped to fit over the other ear with a strap running between them that fits over a user's head or around the user's neck. However, other suitable structures for attaching hearing protection can be utilized with the embodiments of the present disclosure.

The device 100 also includes a third material 110 positioned on a first side of the first material 102. The third material portion 110 can be formed from any suitable material. One example of a suitable material is foam.

However, in some embodiments, the device can have just first and second material portions. As illustrated in the embodiment of FIG. 1, this first material can be a housing of the hearing protector. For example, the first material can be an ear cover portion of the body of the device.

In embodiments of the present disclosure, the body can have multiple portions that provide different sound attention at different decibel ranges. For example, in some embodiments, a first portion of the body can provide sound attenuation at a first decibel range. A second portion can be designed to provide a sound attenuation at a second decibel range.

For instance, the first portion may include a first sound attenuating material and, in some embodiments, a second sound attenuating material (e.g., first and second materials 102 and 106 of FIG. 1). In such an embodiment, the first portion may include an aperture. The use of the aperture changes the sound attenuation characteristics of the first portion with respect to the sound attenuation characteristics of the second portion.

One benefit of such an embodiment can be that the device can be designed to attenuate sound that could be harmful to a user, but allow the user to hear other sounds, such as a project manager giving the user instructions. Through use of varied size, shape, and/or depth of the one or more apertures and/or the materials used to construct the portions of the device, the sound attenuation of the device can be tuned (e.g., during and/or after manufacture, in various embodiments) for different applications where the sound environment may be different and need attenuation at different ranges.

In some embodiments, first and third materials can be directly adjacent to one another or in some embodiments, the materials may have one or more layers provided between them, however, such structures do not affect the scope of the present disclosure.

The device 100 includes one or more apertures 104 formed in the first material 102. In the embodiment illustrated in FIG. 1, the device has three apertures, however, embodiments of the present disclosure can have any number of apertures.

Additionally, the apertures can be of any suitable size. In fact, the diameter, interior shape, and/or depth of the aperture are characteristics that can be utilized to change the sound attenuation characteristics of the aperture.

For example, an aperture of a first diameter may have different attenuation characteristics than one having a second diameter (i.e., larger or smaller). Accordingly, in some embodiments, the device can have multiple apertures and the apertures can be of different sizes, shapes, and/or depths. It should be noted that changes in interior shape can include a change in the shape of any side, top and/or bottom surface of the aperture (i.e., interior cavity formed by the first, second, and/or third materials).

For example, in some embodiments, the device includes multiple apertures formed in at least the first material and at least two of the apertures have different diameters. Such an embodiment will be discussed in more detail below with regard to FIGS. 2A and 2B.

As illustrated in FIG. 1, and discussed above, the device also includes a second material that is positioned over the apertures 104 (e.g., applied on one side surface of the first material 102). In the embodiment of FIG. 1, the material is a thin film 106 that is applied over the surface of the first material 102 and extends over all three apertures provided.

In some embodiments, different materials can be used to cover one or more of the apertures. For example, materials having different attenuation characteristics could be used over different apertures.

Examples of attenuation characteristics include: type of material, thickness, permeability, and flexibility, uniformity of the thickness across the aperture, among others. Such characteristics can be selected to change the sound attenuation of each aperture and, therefore, the device can be tuned to best attenuate sound in particular applications, in some embodiments.

In various embodiments, the second material can be integral with the first material. For example the second and first materials could be formed or bonded together.

In various embodiments, the second material can be removable from the first material and/or replaceable, thereby allowing the sound attenuation characteristics of the device to be changed (or each aperture, in some embodiments) by either removing the material or replacing one piece of material with another piece of material that has one or more different characteristics than the one that was removed.

In some embodiments, the sound attenuating characteristics of one material can be different from one or more of the other materials. For example, in various embodiments, the second material has sound attenuating characteristics that are different from the sound attenuating characteristics of the first material.

In embodiments having three materials, the third material can have sound attenuating characteristics that are different from the sound attenuating characteristics of the first material, in some embodiments. And, in various such embodiments, the third material can have sound attenuating characteristics that are different from the sound attenuating characteristics of the second material.

In some embodiments, such as that illustrated in FIG. 1, a weight can be used to change the attenuating characteristics of the second material (and, thereby, the aperture). For instance, by attaching a weight to the second material, it changes the material's ability to resonate. The weight can be any suitable shape and can be fabricated from any suitable material. For example, the weight can be fabricated from the same material as the second material (e.g., a polymer material). Further, the weight can be affixed to the surface of the second material that is inside the aperture, or can be positioned on the other side of the second material, such that the weight is outside the aperture. In some embodiments, the weight can be removable and/or replaceable, such that the device can be tuned through removal of the weight or use of weights that are different in size, shape, weight, and/or material type.

Figure 2A:
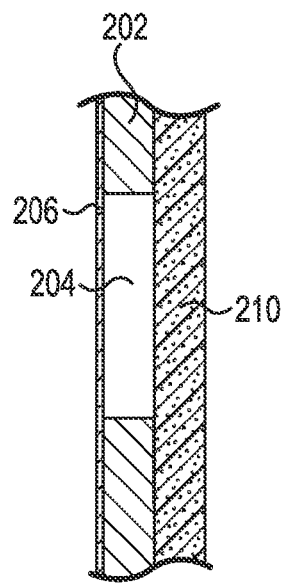
FIG. 2A illustrates a noise attenuating structure in accordance with one or more embodiments of the present disclosure.

FIG. 2A illustrates a noise attenuating structure in accordance with one or more embodiments of the present disclosure. In the embodiment of FIG. 2A, an aperture 204 is illustrated as being formed in a first material 202 and between third material 210 and second material 206.

This structure acts to form a cavity within the aperture which gives this portion of the device a different set of attenuating characteristics than other portions of the device (e.g., a portion having first, second, and/or third material layers, but no aperture formed therein). As discussed above, this can be a second portion of the device that has different sound attenuating characteristics than a first portion and can include an aperture formed between a foam material and a thin film material.

Figure 2B:
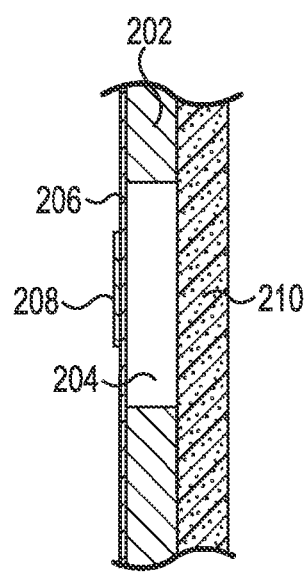
FIG. 2B illustrates another noise attenuating structure in accordance with one or more embodiments of the present disclosure.

FIG. 2B illustrates another noise attenuating structure in accordance with one or more embodiments of the present disclosure. In the embodiment of FIG. 2B, an aperture 204 is illustrated as being formed in a first material 202 and between third material 210 and second material 206. This structure acts to form a cavity within the aperture which gives this portion of the device a different set of attenuating characteristics than one or more other portions of the device.

Additionally, a weight is formed outside of the aperture 204 and defined cavity. However, as discussed above, the weight could be within the aperture and defined cavity, in some embodiments (such as in FIG. 1).

FIG. 3A illustrates another noise attenuating structure in accordance with one or more embodiments of the present disclosure. In the embodiment of FIG. 3A, an aperture is illustrated as being formed in a first material 302 and between third material 310 and second material 306. This structure acts to form a cavity within the aperture which gives this portion of the device a different set of attenuating characteristics than one or more other portions of the device.

In the embodiment of FIG. 3A, the second material 306 is positioned within the aperture that is formed in first material 302. In such embodiments, the second material can be affixed in any suitable manner, such as, mechanical attachment (as shown in FIG. 3A), and/or adhesive attachment, among other suitable attachment mechanisms. In some embodiments, the aperture can extend into a third material 310 (if utilized) and the membrane may also be positioned into the third material via the aperture, in some embodiments.

FIG. 3B illustrates another noise attenuating structure in accordance with one or more embodiments of the present disclosure. In the embodiment of FIG. 3B, an aperture 322 is illustrated as being formed in a first material 302. In this embodiment, the second material 306 is positioned over (i.e. extending across) from an inside surface of the first material 302. The first material is shaped to form a cavity between third material 310 and second material 306.

This structure acts to form a cavity, similar in function to that of previous embodiments, which gives this portion of the device a different set of attenuating characteristics than one or more other portions of the device. In some embodiments, the second material 306 could be positioned over the aperture 322 and attached to the outer surface of the first material 302.

FIG. 3C illustrates another noise attenuating structure in accordance with one or more embodiments of the present disclosure. In the embodiment of FIG. 3C, an aperture 322 is illustrated as being formed in a fourth material 320. This material can be any suitable material for providing an aperture.

In this embodiment, the second material 306 is positioned over (i.e. extending across) from an inside surface of the fourth material 320. In this embodiment, the second material is positioned between the first material 302 and the fourth material 320, however, the embodiments of the present disclosure are not so limited.

In the embodiment of FIG. 3C, the first material is shaped to form a cavity between third material 310 and second material 306. This structure acts to form a cavity, similar in function to that of previous embodiments, which gives this portion of the device a different set of attenuating characteristics than one or more other portions of the device. In some embodiments, the second material 306 could be positioned over the aperture 322 and attached to the outer surface of the fourth material 320.

FIG. 3D illustrates another noise attenuating structure in accordance with one or more embodiments of the present disclosure. In the embodiment of FIG. 3D, an aperture 322 is illustrated as being formed in a first material 302. In this embodiment, the second material 306 is positioned over (i.e. extending across) from an inside surface of the first material 302. The first material is shaped to form a cavity between third material 310 and second material 306.

This structure also acts to form two cavities (i.e., a second cavity between first material 302 and second material 306), that are both similar in function to that of previous embodiments, which gives this portion of the device a different set of attenuating characteristics than one or more other portions of the device. Accordingly, it should be understood that multiple cavities may be positioned in a serial arrangement with respect to the sounds entering the device as is illustrated in FIG. 3D. In some embodiments, the second material 306 could be positioned over the aperture 322 and attached to the outer surface of the first material 302.

FIG. 3E illustrates another noise attenuating structure in accordance with one or more embodiments of the present disclosure. In the embodiment of FIG. 3E, an aperture 322 is illustrated as being formed in a fourth material 320. This material can be any suitable material for providing an aperture.

In this embodiment, the second material 306 is positioned over (i.e. extending across) from an inside surface of the fourth material 320. This embodiment provides that, the second material is positioned between the first material 302 and the fourth material 320, however, the embodiments of the present disclosure are not so limited.

In the embodiment of FIG. 3E, the first material is shaped to form a cavity between third material 310 and second material 306. This structure acts to form two cavities, that, as discussed above, are both similar in function to that of previous embodiments, which gives this portion of the device a different set of attenuating characteristics than one or more other portions of the device. Accordingly, it should be understood that multiple cavities may be positioned in a serial arrangement with respect to the sounds entering the device as is illustrated in FIG. 3E. In some embodiments, the second material 306 could be positioned over the aperture 322 and attached to the outer surface of the fourth material 320.

Figure 4:
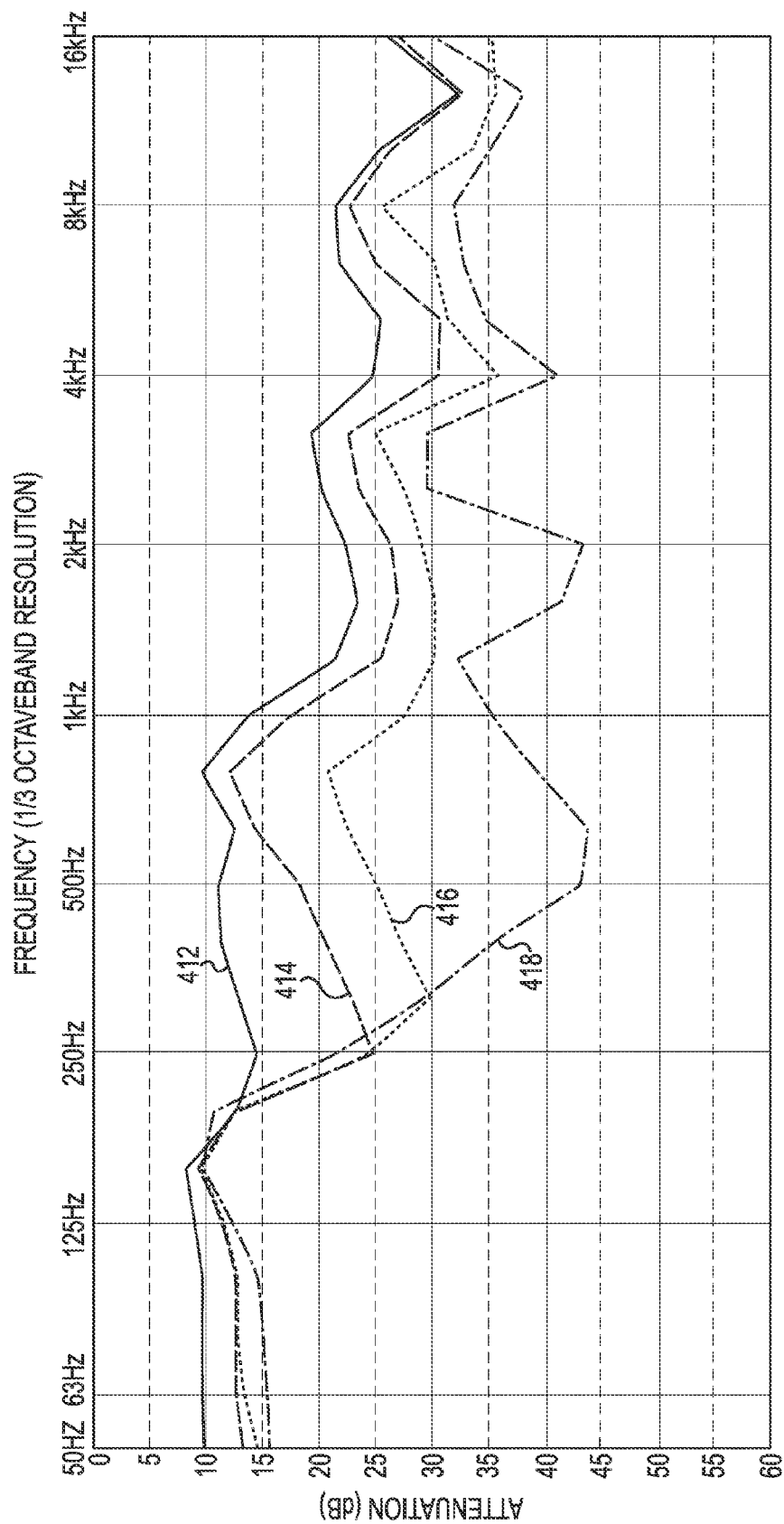
FIG. 4 illustrates a chart showing the noise attenuation using various embodiments of the present disclosure.

FIG. 4 is a chart illustrating noise attenuation of various structures formed in accordance with one or more embodiments of the present disclosure. In this figure, the chart provides attenuation examples, for devices having no apertures at 418, one aperture at 416, two apertures at 414, and three apertures at 412.

As can be seen from this set of examples, the more apertures that were provided on the device, the generally lower the attenuation of the device at certain sound frequency ranges, such as the 250 to 1300 Hz range, while attenuation at other ranges was not as affected, such as 2300 Hz and higher frequencies. In some applications, the illustrated change at higher frequencies can still be viewed as significant and, in some embodiments, the change at higher frequencies can be even greater than is illustrated in the chart.

The illustrated embodiments in the chart also provide some sound attenuation at low frequencies which may be an improvement over devices which provide little to no protection at lower frequencies (e.g., up to 500 Hz). Such embodiments can be useful for allowing the user to hear better at some frequency ranges thereby allowing for better overall user safety with hearing protection, in some applications.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A hearing protection device, comprising:
   a first material, having sound attenuating characteristics, shaped to cover over an ear of a user;
   at least one aperture formed in the first material; and
   a second material positioned over the aperture, wherein the second material is positioned outside the first material.

2. The device of claim 1, wherein the second material has sound attenuating characteristics that are different from the sound attenuating characteristics of the first material.

3. The device of claim 1, wherein the first material forms a portion of a body of the hearing protection device.

4. The device of claim 1, wherein a third material with sound attenuating characteristics is provided inside of the first material.

5. The device of claim 4, wherein the third material has sound attenuating characteristics that are different from the sound attenuating characteristics of the first material.

6. The device of claim 4, wherein the third material has sound attenuating characteristics that are different from sound attenuating characteristics of the second material.

7. The device of claim 1, wherein the second material is a thin film material or membrane.

8. The device of claim 4, wherein the third material is a foam material.

9. A hearing protection device, comprising:
   a first material, having sound attenuating characteristics, and shaped, on a first side, to cover over an ear of a user;
   at least one aperture formed in the first material;
   a second material, having sound attenuating characteristics, positioned over the aperture; and
   a third material comprising foam, having sound attenuating characteristics, positioned inside of the first material.

10. The device of claim 9, wherein the device includes a weight attached to the second material and positioned over the aperture.

11. The device of claim 9, wherein the device includes a weight attached to the second material and positioned between the third material and the second material.

12. The device of claim 10, wherein the weight is removable from the second material.

13. The device of claim 9, wherein the device includes multiple apertures formed in the first material and wherein at least two of the apertures have different diameters.

14. The device of claim 9, wherein the device includes multiple apertures formed in the first material and wherein the apertures are formed between the second material and another material.

15. The device of claim 14, wherein the other material is the third material.

16. A hearing protective device, comprising:
   an ear covering body shaped on a first side to cover an ear of a user, and comprising a first material having sound attenuating characteristics;
   an aperture in the first material;
   a second material having sound attenuating characteristics and positioned over the aperture; and
   a third material having sound attenuating characteristics and positioned inside the first material;
   wherein the third material comprises foam that spans the aperture.

17. The device of claim 16, wherein the second material is a thin film material or membrane.

18. The device of claim 17, wherein the second material is positioned outside the first material.

19. The device of claim 17, further comprising a weight attached to the second material and positioned over the aperture.

20. The device of claim 19, wherein the weight is removable from the second material.

* * * * *